United States Patent

Guldi et al.

[11] Patent Number: 5,841,543
[45] Date of Patent: Nov. 24, 1998

[54] METHOD AND APPARATUS FOR VERIFYING THE PRESENCE OF A MATERIAL APPLIED TO A SUBSTRATE

[75] Inventors: Richard L. Guldi, Dallas; Douglas E. Paradis, Richardson, both of Tex.

[73] Assignee: Texas Instruments Incorporated, Dallas, Tex.

[21] Appl. No.: 401,741

[22] Filed: Mar. 9, 1995

[51] Int. Cl.$^6$ ...................................................... G01N 11/00
[52] U.S. Cl. ...................... 356/394; 250/272; 250/559.39
[58] Field of Search .................................... 356/394, 237; 250/559.39, 559.4, 559.42, 372

[56] References Cited

U.S. PATENT DOCUMENTS 4,421,410  12/1983  Karasaki .................................. 356/237

FOREIGN PATENT DOCUMENTS 61-250546  11/1986  Japan ...................... 356/394
61-250547  11/1986  Japan ...................... 356/394

*Primary Examiner*—F. L. Evans
*Attorney, Agent, or Firm*—W. James Brady, III; Richard L. Donaldson

[57] ABSTRACT

The invention provides a process for evaluating a substrate, such as a wafer of semiconductive material having a semiconductor die at least partially formed thereon, as to the condition of an overlying film, such as an overlying film of photoresist that is applied to the semiconductor die prior to metal etching and ion implantation. The condition of the film is evaluated by exposing at least a portion of the substrate to electromagnetic radiation and evaluating the wave profile of the reflected beam. In instances where it is desirable to evaluate the substrate for the presence or absence of photoresist, ultraviolet or near ultraviolet light having a wavelength of about 240–650 nm can be used, as such wavelengths are strongly absorbed by photoresist. In contrast, areas of the substrate that are not covered by photoresist will not significantly absorb ultraviolet or near ultraviolet radiation. The presence or absence of the film under study can be evaluated by detecting reflected light from the substrate and comparing the detected light to a known profile. When photoresist films are under evaluation, the profile will feature portions of relatively low amplitude, which correspond to absorption of uv due to the presence of photoresist, and portions of relatively high amplitude, which correspond to non-absorption (reflectance) of uv. While the principles of the invention are applicable to single-point testing of a substrate, it is preferable to undertake a multi-point, and more preferably a continuous scan, of at least a portion of the substrate to minimize the occurrence of possibly erroneous results, as could occur from sampling a portion of the substrate that was deliberately not patterned with the film under study.

13 Claims, 2 Drawing Sheets

METHOD AND APPARATUS FOR VERIFYING THE PRESENCE OF A MATERIAL APPLIED TO A SUBSTRATE

TECHNICAL FIELD OF THE INVENTION

The invention relates generally to semiconductor processing, and more particularly to methods and apparatus for confirming the presence of applied, and typically patterned, materials to semiconductor devices at various stages of semiconductor processing.

BACKGROUND OF THE INVENTION

Considerable efforts are expended by semiconductor manufacturers to improve product yield and lessen the frequency of defects in product manufacture. Difficulties in increasing product yield are exacerbated by the marketplace demand for technologically advanced product at reduced prices. For all but a narrow group of specialty product manufacturers, profits are obtained through high volume sales rather than through high profit margins per product. Accordingly, loss of product yield due to errors of manufacturer, is handling and the like impact significantly upon the overall commercial success of the product.

Product yield loss can be experienced at virtually any stage of semiconductor processing. For example, loss can occur as a result of the failure to fully incorporate a process step into the manufacture of the semiconductor device, a deviation from established processing regimen, the use of defective reagents, and the like. Such deficiencies are typically not identified until the completion of device manufacture and random product testing. The identification of a defective product from a given wafer can result in the discard of not only the semiconductor under test, but also the entirety of the wafer and its associated devices, as well as the batch of wafers that were processed in a like manner. Upwards of 500 devices can be manufactured on a single wafer. Moreover, as wafers are typically processed in batches of 15 or more, the identification of a processing defect that relates to the entirety of a batch can result in a considerable economic loss. In such instances, not only does the financial loss relate to the inability to sell manufactured product, there are also considerable losses experienced as a result of expenditure of personnel time, chemical reagents, and processing apparatus all expended on goods that cannot be introduced into commerce.

In view of the foregoing deficiencies in the prior art of semiconductor processing, it would be desirable to provide semiconductor processing methods and apparatus which allow for the confirmation of a properly applied and processed materials, such as patterned photoresist and other applied materials, at various stages of semiconductor processing in a manner which requires minimal interruption in the processing regimen. It would also be desirable to provide methods and apparatus for confirming the presence of a photoresist pattern and other applied materials which do not require physical contact with the semiconductor device incident to evaluation of the device for the presence of the material under study. These and other advantages of the methods and apparatus of the present invention will become apparent by reading the following detailed description and drawings.

SUMMARY OF THE INVENTION

The invention provides a process for evaluating a substrate, such as a wafer of semiconductive material having a semiconductor die at least partially formed thereon, as to the condition of an overlying film, such as an overlying film of photoresist that is applied to the semiconductor die prior to metal etching and ion implantation. The condition of the film is evaluated by exposing at least a portion of the substrate to electromagnetic radiation and evaluating the wave characteristics of the reflected beam.

In instances where it is desirable to evaluate the substrate for the presence or absence of photoresist, ultraviolet or near ultraviolet light having a wavelength of about 240–650 nm can be used, as such wavelengths are strongly absorbed by photoresist. In contrast, areas of the substrate that are not covered by photoresist will not significantly absorb ultraviolet or near ultraviolet radiation. The presence or absence of the film under study can be evaluated by detecting reflected light from the substrate and comparing the detected light to a known profile. In instances where photoresist films are under evaluation, the profile will feature portions of relatively low amplitude, which correspond to absorption of uv due to the presence of photoresist, and portions of relatively high amplitude, which correspond to non-absorption (reflectance) of uv. While the principles of the invention are applicable to single-point testing of a substrate, it is preferable to undertake a multi-point, and more preferably a continuous scan, of at least a portion of the substrate is undertaken to minimize the occurrence of possibly erroneous results, as could occur from sampling a portion of the substrate that was deliberately not patterned with the film under study.

BRIEF DESCRIPTION OF THE DRAWINGS

Embodiments of the invention have been chosen for purposes of illustration and description, and are shown with reference to the accompanying drawings, wherein.

DETAILED DESCRIPTION OF PREFERRED EMBODIMENTS

Figure 1:
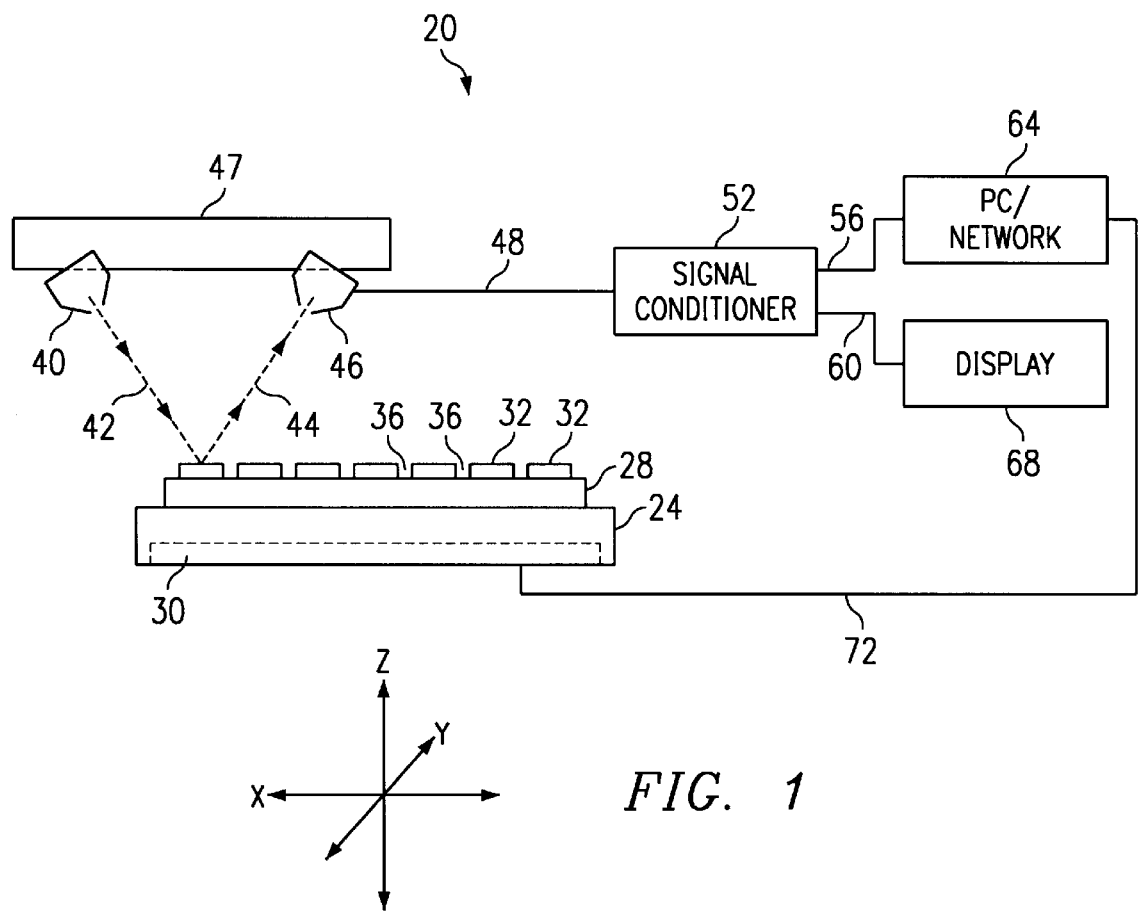
FIG. 1 is a schematic side view of an apparatus for verifying the presence of a resist pattern in accordance with the present invention.

With reference to the drawings, wherein like characters represent corresponding parts throughout the various illustrations, and with particular reference to FIG. 1, there is illustrated in schematic form an applied materials detection system, which is designated generally by reference character 20, that is particularly advantageous for use in the processing of semiconductors. As will be explained in greater detail below, the detection system 20 can be used to detect the presence of a patterned and developed photoresist prior to the implementation of ion implantation, as well as for the detection of the presence of other materials that are used to construct semiconductor devices and other articles of manufacture.

The detection system 20 is comprised generally of a displaceably mounted stage 24, which is provided to support a wafer 28, as illustrated in the drawing. The stage 24 is preferably coupled to appropriate drive system 30 such as a stage motor that is operable to linearly displace the stage along one, and preferably two, horizontal axes, such as "x" and "y" axes illustrated in the drawing. As will be described in more detail below, the invention encompasses the selection and placement onto the stage 24 of a wafer that is preferably representative of a batch of wafers that are at a common stage of wafer processing.

Typically, such wafers are received within wafer boats (not shown) which are used to transport the wafers between processing stations.

Arranged on each wafer 28 is a plurality of dies 32 that can optionally be separated from one another by scribe streets 36, as shown in the drawing. The dies 32 are typically arranged in an organized, grid-like pattern along an upper surface of the wafer, as is understood in the art. A light source 40 is provided to illuminate the dies 32 with a light beam 42 having a prescribed wavelength. In instances where the presence of a developed photoresist is to be evaluated, ultraviolet or near ultraviolet light is desirable because such wavelengths are highly absorbed by the developed photoresist. In a preferred aspect of the invention, a light source such as a mercury vapor light source which is capable of emitting light within a wavelength range of about 240–650 nm is employed to evaluate the wafer dies 32 for the presence of a developed photoresist pattern. At least a portion of the light beam 42 is reflected as a reflected beam 44 from the surface of the wafers 32 and is received by a detector 46 that is operable to generate a signal output in response to receipt of a reflected beam having a prescribed range of wavelengths. The light source 40 and the detector 46 can optionally be secured to a common support surface 47 (as shown) to maintain a predetermined spatial relationship, and the support surface 47 can optionally be mounted for movement along horizontal "x" and "y" axes by coupling to appropriate motor drive and control apparatus (not shown).

Signal output from the detector 46 is directed along path 48 to a signal conditioner 52 that is itself operable to process the detector output signal and generate separate, related outputs that are directed along lines 56 and 60 to PC/network 64 and (optionally) a signal display 68, respectively. The signal conditioner 52 is preferably in the form of automated signal processing circuitry that can be configured as a free-standing component or as a component or subsystem of computer. Signal output from the conditioner 52 to the signal display 68 allows for the generation of suitable visually and/or audibly perceptible signals or alarms in instances where the signal output along line 60 corresponds to a detected beam 44 having undesirable attributes, such as unduly high amplitude or reflectance in instances where the presence of a patterned photoresist is desired. Signal output from the conditioner 52 to the PC/network 64 comprises signal data relating to the reflected light intensity (amplitude) that is received at the detector 46 from the wafer 28 as a wafer under test is evaluated in the x-y plane, as will be described in greater detail below.

Figure 2:
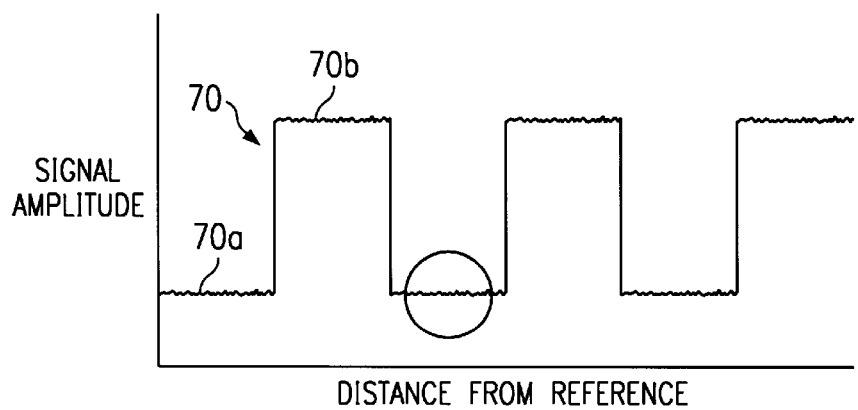
FIG. 2 is an illustrative example of a detector signal trace indicating the presence of a developed photoresist pattern on a wafer.

More particularly, the signal conditioner 52 is operable to evaluate the detector signal emitted for the presence of a bi-level signature 70 of the type illustrated in FIG. 2. As is shown in the drawing figure, the signature 70 is comprised of two discrete segments: a relatively low amplitude signal portion 70a and a relatively high amplitude signal portion 70b. The low amplitude signal portion 70a corresponds to diminished reflectance of the incident beam 42, as would occur from absorption of the incident beam. The higher amplitude portion 70b corresponds to relatively greater reflectance, as would occur in instances of diminished absorption of the incident beam 42. As developed photoresist is highly uv-absorptive, a surface covered by a developed photoresist layer or film would be expected to exhibit a reflectance analogous to signal portion 70a, whereas non-absorptive surfaces, such as those that are not covered by a patterned photoresist, would be expected to exhibit a reflectance analogous to signal portion 70b due to relatively diminished levels of uv absorptance. Minor signal variations, as illustrated in the circle-highlighted portion of FIG. 2, can arise from incident light scattering along the surface topography of the wafer dies 32 as relative motion is imparted between the wafer 28 and the source/detector 40/46. Such relative motion results in the incident beam 42 being directed across one or both coated and uncoated regions, thus giving rise to a reflected beam 44 having corresponding characteristics. Preferably, the incident beam 42 is directed in a continuous motion over the wafer 28 to permit generation of continuous, step-like graphic function of the type depicted in FIG. 2 illustrating the transition between absorbed and substantially non-absorbed signal output from the detector 46; however, discontinuous sampling can be undertaken. When sampling is discontinuous, as in the case of point sampling, it is desirable to obtain detector signal output from at least two different points along the surface of the wafer. Alternatively, the signal conditioner can be operable to evaluate periodicity of the signature 70 in the x- or y-directions, or a combination thereof, as a function of scanned distance to verify that the bi-level pattern signature 70 illustrated in FIG. 2 is repetitive. While such periodicity is not required to discern the presence of a photoresist or other patterned materials under study, the presence of such periodicity assists in the confirmation of the presence of such patterns. Use of an incident beam 42 having a relatively narrow width of ~1 µm, in accordance with a preferred aspect of the invention, allows for the identification of relatively large variations when the beam is scanned across topographical features of the circuit area.

PC/network 64 (FIG. 1) can be coupled to the stage drive system 30 by way of signal line 72 to provide stage drive signal input and to otherwise monitor various performance characteristics of the drive system, as is known in the art. Alternatively, the drive system 30 can be operable independent of the PC/network 64 and detection system 20. PC/network 64 is operable to maintain an inspection history database of sampled wafers, identifying them by appropriate indicia such as date, time, process batch number and other appropriate identification and data parameters. This information can be shared with other components of the network by appropriate communication hardware and protocol. Moreover, the PC/network 64 can be operable to transmit a status deficiency or alarm signal to various processing stations, such as the processing station that applies and develops photoresist. Generation of such a status deficiency or alarm signal allows for the timely implementation of remedial measures to ensure that further faulty photoresist and other patterns under study are not produced. Alternatively, the foregoing status deficiency or alarm signal can be generated by the signal conditioner 52 for communication to the foregoing processing stations. Either of the foregoing status deficiency or alarm signals can be directed to the optional signal display 68 to alert semiconductor processing personnel as to the existence of a possible manufacturing defect in the semiconductor devices 32 of a batch being processed.

In a preferred aspect of the invention, the stage 24 is displaceably mounted and operable through action of the associated stage drive system 30 to position two or more different portions of the wafer upper surface 38, and more particularly, different portions of semiconductor devices 32 under construction, under the beam 42 emitted by the light source 40 so as to permit for sampling from a corresponding number of positions of the wafer upper surface 38 for the detection of developed photoresist or some other material under study. This is preferably accomplished by linearly advancing the stage 24 along one or both of the x- and y-axes while the light source 40 and detector 46 are in operation to render a continuous (line) scan of the type illustrated in FIG. 2. The invention has particular utility, for example, prior to the metal etch step, where it is customary to pattern and develop a photoresist layer to protect metal from etching certain portions of the semiconductor device 32 underlying the photoresist, which portions are to become electrical leads. As such, photoresist following development would ordinarily not be expected to be present in scribe streets, whereas photoresist would be expected to be present along some of the upper surfaces of partially formed semiconductor devices 32.

The photoresist pattern in the scribe streets 36 is normally designed to be developed away in order that metal will be removed by etching in the scribe streets. Removal of the metal from the scribe streets permits sawing of the wafer at a subsequent processing step, incident to die separation, to proceed with minimum damage to the sawing equipment, as sawing through metal is avoided. Development of the photoresist pattern away from the scribe streets 36 facilitates visualization of certain pattern alignment structures or verniers as well as other parametric test structures that are contained in the unused wafer sections defined by the scribe streets.

Movement of the stage 24 so as to permit optical sampling (preferably in a continuous manner) from at least two different locations along the surface of the wafer is desirable to address instances that could give rise to misleading or false signals indicative of the absence of a desired material. Such misleading or false signals can arise, for example, when wafer scribe streets 36 are positioned under the incident light beam 42. Such a condition would result in the generation of a reflected signal 44 to the detector 46 that would, in turn, result in the generation of a signal indicative of lack of photoresist when such is not necessarily by the case with respect to the partially completed semiconductor devices 32 formed along the wafer.

Figure 3:
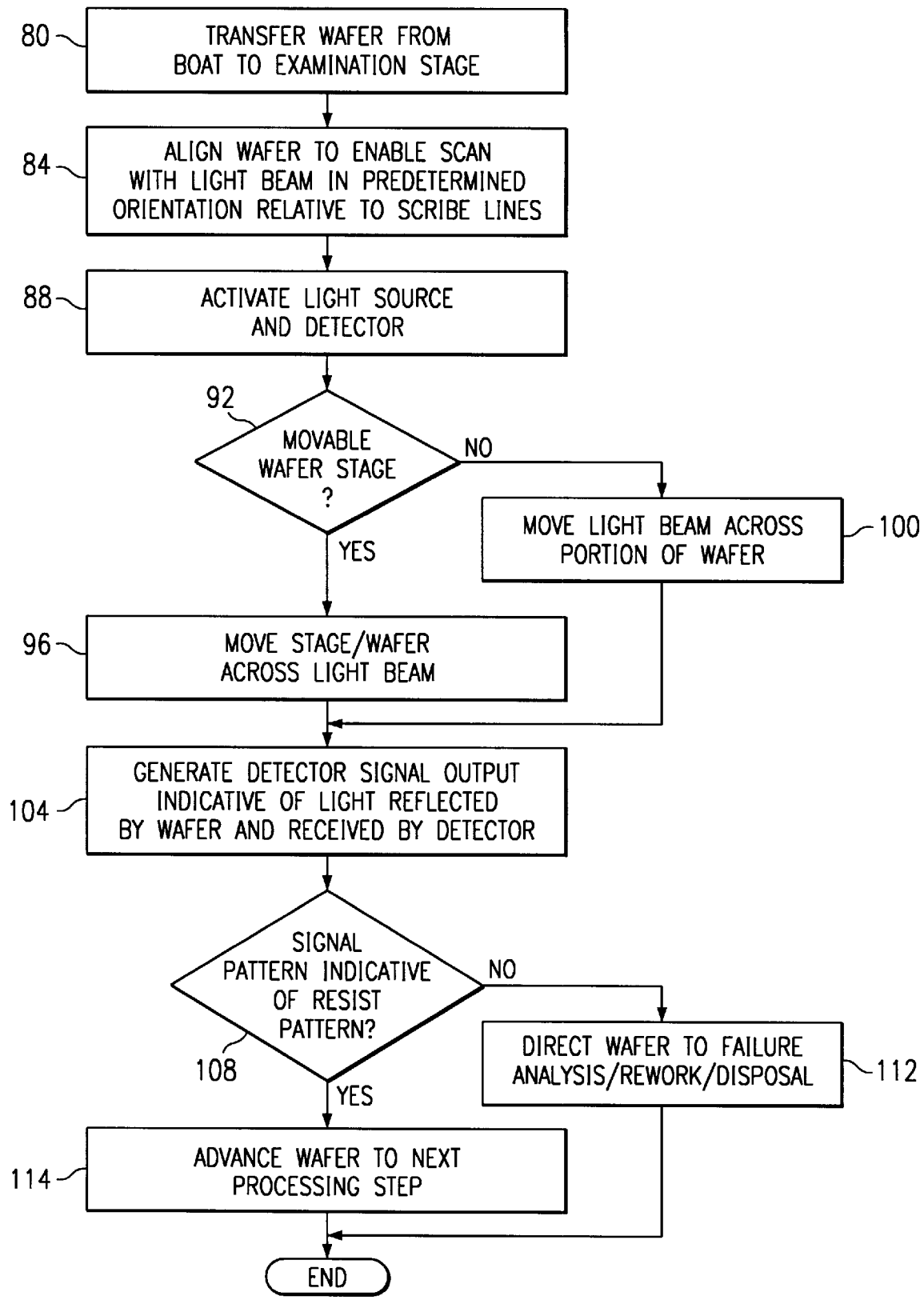
FIG. 3 is a flow diagram of some of the logic steps associated with the practice of the present invention.

The steps involved in the process of the invention are illustrated in FIG. 3. At the outset of this process, wafers 28 that have completed a particular stage of processing, such as conventional photoresist patterning and development, are transferred from their receptacle, typically a wafer boat (not shown), to the stage 24 for examination, as indicated by block 80. The transferred wafer 28 is secured to the stage 24 in an appropriate manner, and can optionally be positioned in a predetermined orientation on the stage 24, such as by alignment of the wafer's flat edge against a suitable stage reference. Preferably, the wafer 28 is mounted to the stage 24 in such fashion that the wafer scribe streets 36 are positioned within the focal plane of the incident light beam 42, as indicated by block 84. Light source 40 is activated (block 88) to generate an incident wafer scan beam 42, and a portion of the incident beam 42 is reflected as a beam 44 that is received by detector 46. Directing the incident beam 42 within a scribe street 36 results in the generation of a relatively high amplitude signature of the type illustrated at 70*b* (FIG. 2), whereas directing the incident beam along a surface patterned with photoresist results in the generation of a relatively low amplitude signature of the type illustrated at 70*a* (FIG. 2), as discussed previously.

The stage 24 is mounted for horizontal movement along at least one, and preferably two, x- and/or y- horizontal axes, relative to the light beam 42 (block 92), thereby directing one or more different portions of the wafer 28 under the emitted light beam 42, as indicated by block 96. As has been explained previously, movement of the stage 24 and wafer 28 received thereon so as to scan at least two different portions of the wafer upper surface 38, and more particularly the devices 32 mounted thereon, with the incident light beam 42 allows for analysis of the reflected beam 44 from a corresponding number of wafer sites. As characteristics of the reflected beam 44, such as reflected beam amplitude, will vary as a consequence of semiconductor processing, the invention provides for the evaluation of the reflected beam 44 for the presence of a desired aspect of semiconductor manufacture, such as a development of a patterned photoresist. In an alternative aspect of the invention, one or both of the light source 40 and detector 46 can be displaceably mounted with respect to a stationary wafer stage 24. In such instances, the incident light beam 42 is directed across an upper portion of the wafer surface 38 so as to encounter at least two different portions of the wafer and thereby diminish the likelihood of receipt of a reflected Seam 44 that could give rise to a false reading of the stage of manufacture of the semiconductor devices, as indicated by block 100.

In either of the foregoing configurations giving rise to relative movement of the stage and light source/detector discussed above, receipt of the reflected beam 44 by the detector 46 gives rise to the generation of a detector signal that is indicative of the monitored characteristic (i.e., amplitude) of the reflected beam 44 (block 104). The generated detector signal is directed to the signal conditioner 52 along line 48 for further processing, such as evaluation of step height, and optionally periodicity, of the reflected beam step function/signature 70 (FIG. 2). For example, photoresist is highly absorptive of ultraviolet radiation. Accordingly, a beam 44 reflected from the surface of dies 32 along which a patterned photoresist has been developed can be expected to provide a low amplitude reflected signal for receipt by the detector 44 due to low reflectance from the photoresist. In contrast, for areas such as scribe streets where photoresist would not be expected to be found, or for areas where patterned photoresist has not developed properly, a high amplitude reflected beam 44 can be expected due to the comparatively high reflectance from the non-photoresist covered surface. As indicated by decision block 108, generation of a detector signal that is indicative of an undesired characteristic, such as the presence of undeveloped photoresist or the absence altogether of photoresist, results in the appropriate "tagging" of the wafer (physical tagging and/or designation in a database within PC/network 64) and its associated production lot as deficient, thereby allowing for direction of the wafer lot to further, appropriate handling measures. Such supplemental handling measures can include failure analysis/rework/disposal or delivery to an appropriate processing station in instances where a processing step was inadvertently omitted or not completed, as indicated by block 112. Additionally, the manufacturing process can be suspended to allow for correction in the manner described previously of the problem giving rise to the identified deficiency. In contrast, a favorable outcome from decision block 108 confirms the presence of the desired parameter, such as development of a patterned photoresist, and allows for appropriate characterization of the wafer 28 and its associated production lot. Such a favorable outcome allows for advancement of the production lot to the next stage of semiconductor processing, as indicated by block 116.

The foregoing process therefor provides a readily implementable and cost-effective process for expediently and non-destructively evaluating semiconductor devices undergoing manufacture at various stages of the manufacturing process. In instances where an unfavorable outcome of this process has been obtained, appropriate measures, such as initial or reapplication of inappropriate material, failure analysis, and the like can be implemented, preferably at a point prior to packaging, thereby avoiding altogether the relatively considerable cost of packaging defective semiconductor devices.

Those skilled in the art to which the invention relates will appreciate that other substitutions and modifications can be made to the described embodiment, without departing from the spirit and scope of the invention as defined by the claims below. For example, the invention can be incorporated into a variety of semiconductor processing steps in addition to the pre-ion implant and metal etch steps discussed above. Moreover, while the foregoing detailed description has been directed to the art of semiconductor manufacture, the teachings of the present invention are likewise applicable to other areas of manufacture, such as metallurgy, the application of finishes and surface coatings, and the like. Lastly, while the use of ultraviolet and near ultraviolet light has been discussed, the teachings of the present invention are applicable to a wide range of visually perceptible and non-visually perceptible wavelengths, particularly when one desires to inspect for the presence of a pattern that is comprised of layers which have strong absorption of light of a particular wavelength range, as is the case with photoresist and its absorbtion of light in the ultraviolet and near ultraviolet range.

What is claimed is:

1. A process for evaluating a film overlying a substrate, comprising the steps of:
   a. providing a substrate having a surface which supports a plurality of electronic circuit components being assembled upon said substrate;
   b. applying a film in overlying relation to at least one of a portion of said substrate and some of said plurality of circuit components;
   c. providing a single light source and directing an incident light beam from said source at a plurality of positions along said substrate;
   d. generating from each of said substrate positions a reflected beam, each of said reflected beams having a profile that is representative of a feature of the position from which the beam is reflected, said incident and reflected beams traveling along substantially non-overlapping paths;
   e. detecting at least one of said reflected beams; and
   f. comparing the profile of each of said detected beams with a reference profile stored in memory.

2. The process according to claim 1, further comprising the step of imparting relative motion between said substrate and said incident light beam and detecting said reflected beam during at least a portion of said relative motion.

3. The process according to claim 1, further comprising the step of generating an alarm signal if the reflected beam profile differs from said reference profile by an amount in excess of a predetermined threshold value.

4. The process according to claim 1, wherein said profile is an amplitude profile and said comparison provides an indication of light absorption by at least one of said surface and said plurality of circuit components.

5. The process according to claim 4, wherein said incident light beam has a wavelength of from about 240 nm to about 650 nm.

6. The process according to claim 1, further comprising the step of imparting relative motion between said light source and said substrate.

7. The process according to claim 1, wherein said substrate is a wafer of semiconductor material.

8. The process according to claim 7, wherein said film is comprised of one of a photoresist material or a metal-containing material.

9. The process according to claim 1, further comprising the step of automatically conveying said substrate to a predetermined next processing station following said comparison step.

10. The process according to claim 1, wherein at least one of said positions includes a portion of one of said circuit components.

11. A process for evaluating a film overlying a semiconductor substrate, comprising the steps of:
   a. providing a substrate formed of a semiconductor material, said substrate having a surface which supports a plurality of electronic circuit components that are being assembled upon said substrate;
   b. applying a patterned film in overlying relation to at least a portion of said substrate and some of said plurality of circuit components;
   c. advancing said substrate through an incident light beam to illuminate a plurality of positions along said substrate;
   d. generating from each of said substrate positions a reflected beam, each of said reflected beams having a profile that is representative of a feature of the position from which the beam is reflected, said incident and reflected beams traveling along substantially non-overlapping paths;
   e. detecting at least one of said reflected beams; and
   f. comparing the profile of each of said detected beams with a reference profile stored in memory.

12. The process according to claim 11, wherein at least one of said positions includes a portion of one of said circuit components.

13. The process according to claim 11, wherein said incident light beam has a wavelength of from about 240 nm to about 650 nm.

* * * * *